United States Patent [19]

Turkevich et al.

[11] Patent Number: 5,063,301
[45] Date of Patent: Nov. 5, 1991

[54] NONINVASIVE METHOD AND APPARATUS USING COHERENT BACKSCATTERING FOR PROCESS CONTROL

[75] Inventors: Leonid A. Turkevich, Hudson; Kee-Ju Choi, Euclid, both of Ohio

[73] Assignee: The Standard Oil Company, Cleveland, Ohio

[21] Appl. No.: 454,367

[22] Filed: Dec. 21, 1989

[51] Int. Cl.⁵ .............................. G01N 15/06
[52] U.S. Cl. .................... 250/574; 356/336; 356/342
[58] Field of Search ............ 356/336, 342, 351; 250/574

[56] References Cited

U.S. PATENT DOCUMENTS

| | | | |
|---|---|---|---|
| 4,017,186 | 4/1977 | Shofner | 356/342 |
| 4,140,395 | 2/1979 | Kreikebaum | 356/336 |
| 4,251,333 | 2/1981 | Hirleman, Jr. | 250/575 |
| 4,338,030 | 7/1982 | Loos | 356/336 |
| 4,355,897 | 10/1982 | Kaye | 250/574 |
| 4,361,403 | 11/1982 | Loos | 356/336 |
| 4,375,334 | 3/1983 | Gerber | 356/336 |
| 4,387,993 | 6/1983 | Adrian | 356/336 |
| 4,492,467 | 1/1985 | Drain et al. | 356/336 |
| 4,871,251 | 10/1989 | Preikschat et al. | 356/336 |

OTHER PUBLICATIONS

Ho et al., "Particle Size Measuring Device in Real Time for Dense Particulate Systems", *Applied Optics, vol. 17, No. 4, 2/78, pp. 631-634.*
Lagendijk et al; "Localization of Light: The Quest for the White Hole;" *Physica;* 140A (1986), pp. 183-190.
Cwilich et al.; "Rayleigh Scattering and Weak Localization: Geometric Effects and Fluctuations;" *Physical Review B;* vol. 35, No. 13, pp. 6517-6520 (May 1987).
*Light Scattering,* Physics 76, Spring 1986, "Excert from Lab Manual Used Dartmouth College (author W. T. Doyle), obtained by L.T." (sic).

Primary Examiner—Davis L. Willis
Assistant Examiner—Michael Messinger
Attorney, Agent, or Firm—Larry W. Evans; Joseph G. Curatolo

[57] ABSTRACT

A method and apparatus for the noninvasive real-time characterization of samples using coherent backscattering is disclosed. The sample is illuminated by a laser, and the radiation that is coherently backscattered is measured. The line width or line shape of the coherent backscattered radiation, or in some cases just the existence of coherent backscatter, is then used to characterize the sample under test. This characterization is then used for the real time control of a process acting upon the sample.

9 Claims, 7 Drawing Sheets

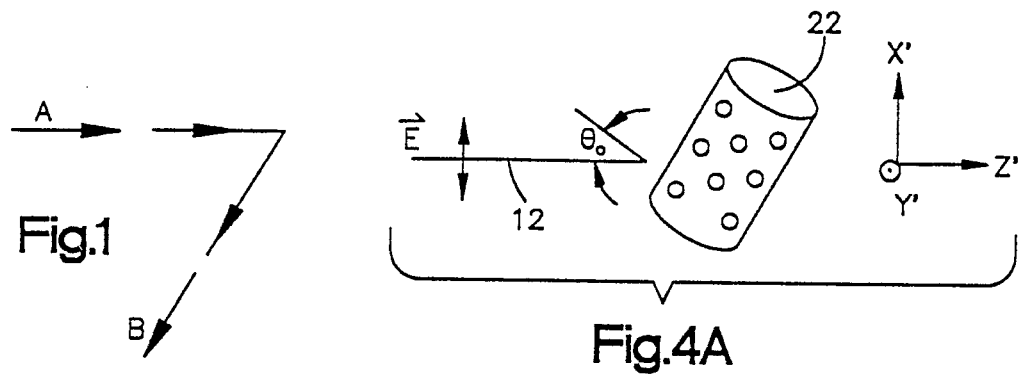
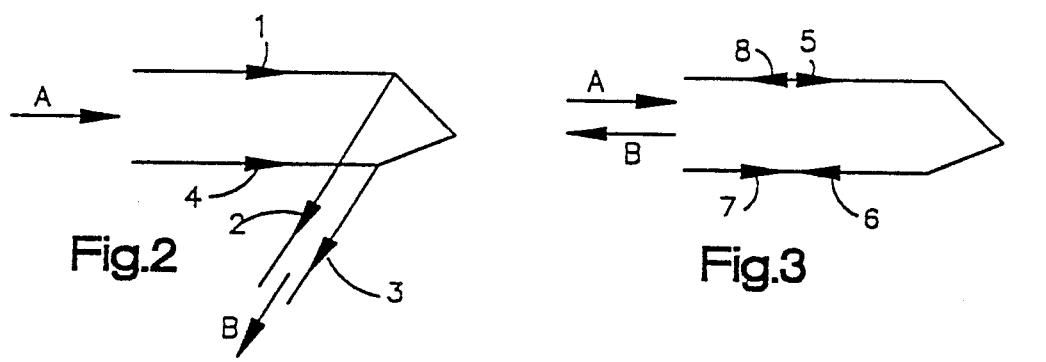
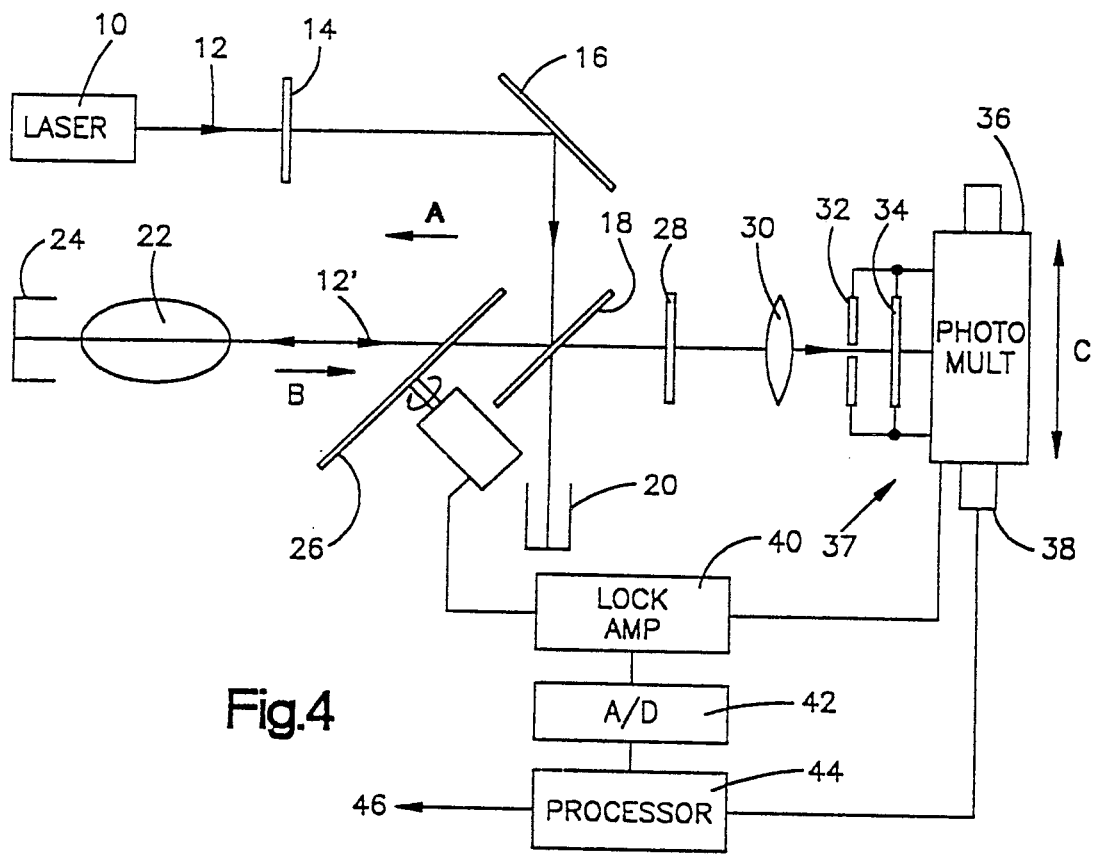

NONINVASIVE METHOD AND APPARATUS USING COHERENT BACKSCATTERING FOR PROCESS CONTROL

BACKGROUND OF THE INVENTION

This invention relates to a method and apparatus for utilizing coherent backscattering to measure characteristics of a sample and to control a manufacturing process in response to the measured characteristic.

Various optical methods have been employed to measure the size or concentration of particles in some form of suspension. These include microscopic inspection of the sample, determination of the extinction coefficient, turbidity, dissymmetry and bulk light scattering in the forward direction.

Light scattering methods are attractive, as they are noninvasive, only optical access to the sample being required. However, bulk light scattering requires low concentration suspensions, as the light must be able to propagate through the sample. In many cases this necessitates dilution, which is time-consuming and which may, in itself, unpredictably alter the properties to be measured.

Other methods such as sieving, membrane permeation, centrifugation and sedimentation not only require a test sample to be drawn from the bulk sample, but also by their nature they inherently require significant time to perform, typically ranging from tens of minutes to hours. It is thus not possible to incorporate these methods into a process control function.

The present invention makes use of coherent backscattering to determine characteristics of the sample. Not only is the method disclosed noninvasive, but it works well on non-dilute suspensions and even opaque materials, and requires, at most, a few minutes to perform.

Electromagnetic radiation or light incident on a sample from a direction A may scatter into an arbitrary direction B (FIG. 1). For dilute samples, the scattered light detected in direction B will have experienced only a single scattering event within the sample. Such dilute samples will not exhibit the coherent backscattering phenomenon.

If the sample is non-dilute, the scattered light detected in direction B may have experienced several scattering events within the sample. FIG. 2 shows three such trajectories which contribute to the light detected in direction B. One trajectory arises from the ray 1, in direction A, which undergoes one scattering event and is redirected along the ray 2. A second trajectory arises from the same ray 1, which undergoes three scattering events, ultimately redirected along the ray 3. A third trajectory arises from the ray 4, in direction A, which undergoes one scattering event and is also redirected along the ray 3.

As the path lengths of these trajectories are uncorrelated, the phases associated with these trajectories are uncorrelated. The total light detected in the arbitrary direction B, being the sum over all such possible trajectories, exhibits no special interference effect, since the uncorrelated phases average out.

However, a special interference phenomenon may occur when the direction B is at (or near) incident direction A. In this case, the trajectories *always* occur in pairs (one being the time-reverse of the other), where each member of the pair possesses identical path length. The phases associated with these time-reversed trajectories are thus identical, and these two trajectories always constructively interfere.

FIG. 3 shows two such trajectories. The first trajectory arises from the ray 5, in direction A, which undergoes three scattering events and is redirected (ray 6) in direction B. The second trajectory arises from the ray 7, in direction A, which undergoes the same three scattering events (but in reverse order) and is redirected (ray 8) in direction B. The only difference between these two trajectories is their direction with respect to time (i.e. the sequence of their scattering events); the path length of these two trajectories is identical. Thus these two paths always constructively interfere. Furthermore, *every* trajectory from incident direction A, which scatters within the sample and ultimately is redirected to the backscattering direction B, has such a time-reversed trajectory with identical path length. Hence, every such path has a time-reversed path with which it constructively interferes. The observed intensity scattered into the backscattered direction B is thus enhanced, by this constructive interference effect, above its classical value.

If coherent backscattering occurs in a sample, the increased intensity occurs not only at the incident angle, but also, to a reduced degree, within some angle off the incident angle. The range of the angle in which the effect occurs is called the line width of the coherent backscattering and the coherent backscattering intensity as a function of the angle is referred to as the line shape.

This line width, $\Delta\theta$, is a function of the scattering mean-free-path, $L$, of light in the random medium. In the case where $L$ is very much greater than $\lambda$, the wavelength of the light in the sample, $\Delta\theta$ is on the order of $\lambda/L$ both for liquid suspensions (e.g., polystyrene spheres in water) and, under special conditions, for particulate solids (e.g., network of colloidal $SiO_2$, or $BaSO_4$ microparticles).

The mean-free-path is, in turn, a function of the size and concentration of scatterers in the sample. In the above examples, $L = 1/n\sigma$, where $n$ is the number density of scatterers and $\sigma$ is the relevant elastic scattering cross-section of a single scatterer. It is thus possible to obtain this elastic scattering cross section, $\sigma$, for a given concentration of scatterers by measuring the mean-free-path, $L$, in coherent backscattering. Similarly, it is possible, if this elastic scattering cross section is known, to obtain the concentration of scatterers by measuring the mean-free-path, $L$, in coherent backscattering. Since the elastic scattering cross section is a known (usually previously measured) function of the size of the scatterer, it is thus possible to obtain the particle size for a given concentration of scatterers or the concentration for a given size scatterer by measuring the mean-free-path, $L$, in coherent backscattering.

While, even for monodisperse, well-characterized samples, it has proved difficult to calculate the relevant elastic scattering cross section, as a function of the particle size from first principles, where this is needed, this can be measured on test samples. Nonetheless, the relationship, $L = 1/n\sigma$, still obtains. For polydisperse samples, the relevant elastic scattering cross section also depends on some moment of the distribution in particle size, and again one would perform calibration experiments. Similarly, if the scatterers are nonspherical, one does not calculate the relevant scattering cross section but, rather, performs calibration experiments.

Again, for most applications, while $L = 1/n\sigma$, the theoretical dependence of the relevant elastic scattering cross section, $\sigma$, on the particle size is unknown. Nevertheless, as disclosed herein, coherent backscattering and its associated line shape can often be observed and measured.

SUMMARY OF THE INVENTION

The present invention is a method and apparatus for controlling a process. This is done by determining characteristics of a sample from the process by comparing the coherent backscattering intensity to that expected or to that of known samples or, in some cases, the occurrence of the coherent backscattering itself indicates the desired characteristic. The characteristic measured is then used to control a process acting upon the sample.

The disclosed method is nonintrusive and can be performed in real time. A variety of samples can be investigated as long as coherent backscatter is a measure of some desired characteristic.

The process control apparatus comprises means for illuminating a sample from a process, means for measuring the line shape for the radiation that is coherently backscattered from the sample and means for providing control signals to the process in response to the measured line shape.

The control signals can be indicative of the size of particles in the sample, the concentration of particles in the sample, precipitation in the sample, fluid phase separation in the sample, foam in the sample, or of the identity of the sample.

BRIEF DESCRIPTION OF THE DRAWINGS

FIG. 1 is a schematic diagram of single scattering in a dilute sample.

FIG. 2 is a schematic diagram of multiple scattering in a non-dilute sample.

FIG. 3 is a schematic diagram of coherent backscattering in a non-dilute sample.

FIG. 4 is a schematic diagram of an apparatus for measuring coherent backscattering from a sample.

FIG. 4A is a schematic diagram showing the geometry of the sample and illuminating beam relative to the coordinate system employed in the line shape calculation.

DESCRIPTION OF THE PREFERRED EMBODIMENT

Figure 5:
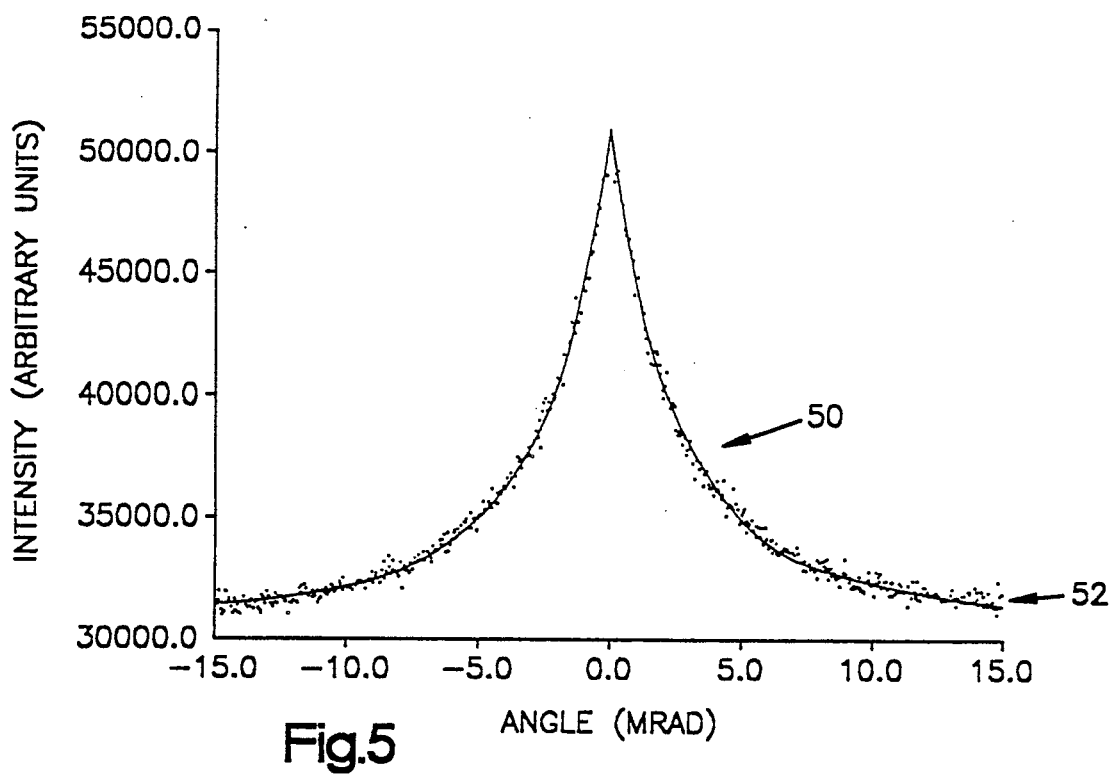
FIG. 5 is a plot of a characteristic coherent backscattering intensity (as a function of backscattering angle) for an aqueous suspension of (0.2 micron diameters) polystyrene spheres (volume fraction = 10%). The solid line is the fitted (theoretical) coherent backscattering line shape.

FIG. 4 shows an apparatus according to the invention. A laser 10 provides a linearly polarized light beam 12. The laser 10 may, for example, provide 50-100 milliwatts at a wavelength of 5145 Angstroms and be polarized perpendicular to the plane of FIG. 4. In practice, the wavelength of the beam 12 is chosen to be compatible with the sample to be investigated. A particular sample may be heavily absorptive at one wavelength, but produce excellent results at a different wavelength.

The light beam 12 passes through a spatial filter/beam expander 14. The filter 14 gives the beam 12 a Gaussian beam profile and expands the beam, for example, by a factor of five. The diameter of the beam 12 after passing through the filter 14 may, for example, be 3 mm.

By expanding the beam, the resolution of the instrument is improved. The original beam is diverging, and the cone of this divergence limits the angular resolution; by expanding the beam waist, the cone of this divergence is reduced.

A mirror 16 directs the beam 12 towards a beam splitter 18. A fraction, typically half, of the beam 12 continues through the splitter 18 and is absorbed by a beam dump 20. The remaining fraction of the beam 12 is reflected by the splitter 18 in direction A where it illuminates the sample 22. Any portion of the beam 12 that continues through the sample 22 is absorbed by a beam dump 24. The sample 22 may, for example, be contained within a transparent glass tube, the axis of which may be advantageously oriented so that the beam 12 is not normal to the walls of the tube. The sample is thus illuminated with p-polarization.

A portion of the beam 12 is reflected from the sample 22 directly back along the incident direction. This scattered beam 12' travels in direction B back to the splitter 18. Directions A and B being direct opposites of each other, the necessary condition for coherent backscattering is achieved.

A chopper 26 periodically interrupts the beams 12, 12' (e.g., 50% on, 50% off at approximately 200 Hz) to aid in detecting the signal of interest as explained below. The beam 12' is split by the splitter 18. The transmitted portion passes through a polarizer 28 which is oriented so as to transmit only the portion of the beam 12' that is polarized parallel to the portion of the beam 12 incident on the sample 22 (in this example, normal to the plane of FIG. 4).

A lens 30 focuses the beam 12' on a pinhole 32. The lens 30 may, for example, have a focal length of 40 cm and the pinhole 32 be located at the focal point. The pinhole 32 may, for example, be 50 microns in diameter.

The distance between the sample 22 and the lens 30 is less than the focal length of the lens, for example, 15 cm.

After exiting the pinhole 32, the beam 12' strikes a beam diffuser 34. In this example, the beam 12' has a diameter of 50 microns when it strikes the diffuser 34. The diffuser 34 may be advantageously constructed of a translucent plastic slab about 1/32" thick.

The beam 12' is diffused by the diffuser 34 and illuminates a photomultiplier 36, which, for example, may be located about ½" from the pinhole 32. This diffusing of the beam 12' overcomes errors from any spatial inhomogeneities in the detection surface of the photomultiplier 36.

The pinhole 32, the diffuser 34 and the photomultiplier 36 form a scanning assembly 37. The scanning assembly 37 is translatable along direction C (perpendicular to the beam 12' and parallel to the plane of FIG. 4) by actuation of a translation stage 38. The translation range may, for example, be approximately 1" about the center of the beam 12'.

By diffusing the beam, the photomultiplier 36 only detects a certain fraction of the backscattered intensity; however, as the photomultiplier and pinhole are translated together, this detection efficiency is constant over the angular scan.

If the translation direction is not accurately aligned perpendicular to the direction of the beam 12', then the variation in acceptance angle through the pinhole 32 results in a sloping background intensity. This can be corrected in the curve-fitting and data analysis.

To advantageously minimize specular reflections, the sample 22 is tilted from the direction normal to the beams 12, 12'. An angle of 45° in a plane normal to the plane of the beams 12, 12' has been found to provide good results. This is close to the Brewster angle, $\theta_B \sim 55°$, for the air/glass interface, since the sample is typically contained in a glass, or quartz, vessel or test tube.

Tilting the chopper 26 (for example at 45° as shown) also improves performance as direct reflection from the chopper wheel is minimized. The reduction of reflection from the chopper wheel is particularly important in those cases where the sample is only weakly scattering and does not yield a large coherent backscattering signal. Also, multiple reflections are reduced if the beam splitter 18 is wedge-shaped (e.g., 3°, not shown) in the plane of the beam 12, 12' and an antireflection coating is applied to the side closest to the sample 22. The beam splitter does not need to be 50:50; the front surface reflection can vary between 10% and 90% without significantly altering the sensitivity.

The chopper 26 provides a reference signal (synchronous with the chop rate) to a lock-in amplifier 40 (e.g., Princeton Applied Research Model 124). The detected signal from the photomultiplier 36 is also input as the signal to the lock-in amplifier 40. The amplifier 40 then synchronously detects the signal and supplies the signal to an analog to digital convertor 42. This synchronous detection allows separating the signal of interest out of background illumination. The digitized detected signal from the converter 42 is then provided as an input to a processor 44. The processor 44 both controls the translation stage 38 and provides an output 46 for controlling a manufacturing process in response to the coherent backscattering from the sample 22. The processor 44 may, for example, be a general purpose computer or a dedicated microprocessor-based system.

In operation, the sample 22 is illuminated by the beam 12 and the backscattering intensity of the beam 12' from the sample 22 is detected by the photomultiplier 36. The scanning assembly 37 is translated about the center of the beam 12' along direction C by the translation stage 38. The translation stage 38 is controlled by the processor 44. As the scanning assembly 37 is translated, the detected intensity of the beam 12' provided by the photomultiplier 36 is modulated by the chopper 26. The lock-in amplifier 20 provides the detected intensities to the analog to digital converter 42. The processor 44 analyzes the measured intensities as a function of the translation of the scanning assembly 37. The processor 44 then provides an output 46 for controlling a manufacturing process in response to the coherent backscattering from the sample 22.

As an example, the output 46 may be the measured coherent backscattering intensities as shown in FIG. 5 (the translation of the photomultiplier 36 is expressed as milliradians from the directly backward direction). This example is from an aqueous suspension (volume fraction = 10%) of monodisperse polystyrene spheres (diameter = 0.2 microns). As is expected for a sample that exhibits coherent backscatter, the intensity in the backward direction (curve 50) is substantially enhanced above the incoherently scattered radiation which is approximately at the level 52. The solid line is the theoretical coherent backscattering line shape, which, when fit to the measured coherent backscattering intensity, yields the mean-free-path, L, of scattering.

To fit the measured intensity to the theoretical line shape, the processor 44 finds the best fit for the equation for the line shape.

The general expression for the line shape (detected light intensity, J, in a particular direction) is given (Cwilich & Stephen, *Phys. Rev. B* 35 6517 (1987)) by the following sum of 6 terms (using their notation):

$$J = J_1 + J_2 + J_3 + J_4 + J_5 + J_6$$

where $J_1 = 1$ $J_2 = [(1 + Q_\perp L_0)^2 + Q_z^2 L_0^2]^{-1}$ $J_3 = (20/9)(1 - 3\cos^2\theta_0 \sin^2\theta_0) I_Q(0,0,7/9)$ $J_4 = (14/9)(1 - 3\cos^2\theta_0 \sin^2\theta_0) I_Q(7/9, 7/9, 7/9)$ $J_5 = (20/3) \cos^2\theta_0 \sin^2\theta_0 I_Q(0,0,13/21)$ $J_6 = (14/3) \cos^2\theta_0 \sin^2\theta_0 I_Q(13/21, 23/21, 13/21)$ where the function $$I_Q(b_1, b_2, b_3) = b_3^{-1} \{[1 + (\cos\theta_0/\sqrt{b_3})(1 + b_1 Q_x^2 L^2 + b_2 Q_y^2 L^2)^{\frac{1}{2}}]^2 + Q_z^2 L_0^2\}^{-1}$$

and where the momentum transfer is given by $Q_x = k \cos\theta_0 \sin\theta' \cos\phi'$ $Q_y = k \sin\theta' \sin\phi'$ $Q_z = k \sin\theta_0 \sin\theta' \cos\phi'$ $Q_\perp = (Q_x^2 + Q_y^2)^{\frac{1}{2}}$ where $k = 2\pi/\lambda$ is the wavenumber of the light, L is the mean-free-path (the parameter which we attempt to fit to the measured data), $L_0 = L \cos\theta_0$. The terms $J_1$, $J_3$, $J_5$ are independent of angle. Thus, when fitting, if a constant background is allowed to float, these terms are subsumed into the floating background. In what follows, we define $\eta = k L |\sin\theta'|$.

In our usual geometry (see FIG. 4A), the incident beam is horizontal ($\vec{k}_{inc}$ is oriented along the z' direction) and is polarized vertically ($\vec{E}$ is oriented along the x' direction).

If the scattered light is detected in a horizontal scan (which is the usual configuration if the detector is physically translated with a translation stage 38, as shown in FIG. 4)

$$\vec{Q} = k \sin\theta' \hat{e}_y$$

$$Q_\perp = k |\sin\theta'|$$

and the function $I_Q(b_1, b_2, b_3)$ takes the form $$I_Q^{(H)}(b_1,b_2,b_3) = b_3^{-1}[1+(\cos\theta_0/\sqrt{b_3})(1+b_2 k^2 L^2 \sin^2\theta')^{\frac{1}{2}}]^{-2}.$$

Thus, a horizontal scan fits to a line shape given by $$J_1 = 1$$

$$J_2 = [1+\eta\cos\theta_0]^{-2}$$

$$J_3 = (20/9)(1-3\cos^2\theta_0\sin^2\theta_0)[\sqrt{(7/9)}+\cos\theta_0]^{-2}$$

$$J_4 = (14/9)(1-3\cos^2\theta_0\sin^2\theta_0)[\sqrt{(7/9)}+\cos\theta_0(1+7\eta^2/9)^{\frac{1}{2}}]^{-2}$$

$$J_5 = (20/3)\cos^2\theta_0\sin^2\theta_0[\sqrt{(13/21)}+\cos\theta_0]^{-2}$$

$$J_6 = (14/3)\cos^2\theta_0\sin^2\theta_0[\sqrt{(13/21)}+\cos\theta_0(1+23\eta^2/21)^{\frac{1}{2}}]^{-2}.$$

As a specific example, if the sample is tilted by $\theta_0 = 45°$ (which is the tilt angle we usually employ), $$J_1 = 1$$

$$J_2 = [1+\eta/\sqrt{2}]^{-2}$$

$$J_3 = (5/9)[\sqrt{(7/9)}+\sqrt{(\frac{1}{2})}]^{-2}$$

$$J_4 = (7/18)[\sqrt{(7/9)}+\sqrt{(\frac{1}{2})}(1+7\eta^2/9)^{\frac{1}{2}}]^{-2}$$

$$J_5 = (5/3)[\sqrt{(13/21)}+\sqrt{(\frac{1}{2})}]^{-2}$$

$$J_6 = (7/6)[\sqrt{(13/21)}+\sqrt{(\frac{1}{2})}(1+23\eta^2/21)^{\frac{1}{2}}]^{-2}.$$

If the scattered light is detected in a vertical scan (which is another possible configuration if the translation stage 38 raises and lowers the detector)

$$\vec{Q} = k(\cos\theta_0 \sin\theta' \hat{e}_x + \sin\theta' \hat{e}_y + \sin\theta_0 \sin\theta' \hat{e}_z)$$

$$Q_\perp = k(1+\cos^2\theta_0)^{\frac{1}{2}}|\sin\theta'|$$

and the function $I_Q(b_1, b_2, b_3)$ takes the form $$I_Q^{(V)}(b_1,b_2,b_3) = b_3^{-1}x$$

$$x\{[1+(\cos\theta_0/\sqrt{b_3})(1+b_1 k^2 L^2 \cos^2\theta_0 \sin^2\theta' + b_2 k^2 L^2 \sin^2\theta')^{\frac{1}{2}}]^2 + k^2 L^2 \cos^2\theta_0 \sin^2\theta'\}^{-1}.$$

Thus, a vertical scan fits to a line shape given by $$J_1 = 1$$

$$J_2 = [(1+\cos\theta_0\sqrt{(1+\cos^2\theta_0)}\eta)^2 + \sin^2\theta_0\cos^2\theta_0\eta^2]^{-1}$$

$$J_3 = (20/9)(1-3\cos^2\theta_0\sin^2\theta_0)[\sqrt{(7/9)}+\cos\theta_0]^{-2}$$

$$J_4 = (14/9)(1-3\cos^2\theta_0\sin^2\theta_0)x$$

$$x\{[\sqrt{(7/9)}+\cos\theta_0(1+(7\eta^2/9)[1+\cos^2\theta_0])^{\frac{1}{2}}]^2 + (7/9)\sin^2\theta_0\cos^2\theta_0\eta^2\}^{-1}$$

$$J_5 = (20/3)\sin^2\theta_0\cos^2\theta_0[\sqrt{(13/21)}+\cos\theta_0]^{-2}$$

$$J_6 = (14/3)\sin^2\theta_0\cos^2\theta_0 x$$

$$x\{[\sqrt{(13/21)}+\cos\theta_0(1+\eta^2[(13/21)\cos^2\theta_0+(23/21)])^{\frac{1}{2}}]^2 + (13/21)\sin^2\theta_0\cos^2\theta_0\eta^2\}^{-1}$$

As a specific example, if the sample is tilted by $\theta_0 = 45°$ (which is the angle we usually employ), $$J_1 = 1$$

$$J_2 = [(1+\sqrt{3\eta/2})^2 + \eta^2/4]^{-1}$$

$$J_3 = (5/9)[\sqrt{(7/9)}+\sqrt{(\frac{1}{2})}]^{-2}$$

$$J_4 = (7/18)\{[\sqrt{(7/9)}+\sqrt{(\frac{1}{2})}(1+7\eta^2/6)^{\frac{1}{2}}]^2 + 7\eta^2/36\}^{-1}$$

$$J_5 = (5/3)[\sqrt{(13/21)}+\sqrt{(\frac{1}{2})}]^{-2}$$

$$J_6 = (7/6)\{[\sqrt{(\frac{1}{2})}(1+59\eta^2/42)^{\frac{1}{2}}]^2 + 13\eta^2/84\}^{-1}.$$

While line widths matching theoretical calculations can be achieved for many particulate suspensions (e.g., polystyrene spheres in water and a network of colloidal $SiO_2$, or $BaSO_4$ microparticles), coherent backscattering can provide useful information about a sample even if no accurate mathematical model exists. An additional alternative is to compare the measured line shape to that of calibration samples with known characteristics.

Figure 6:
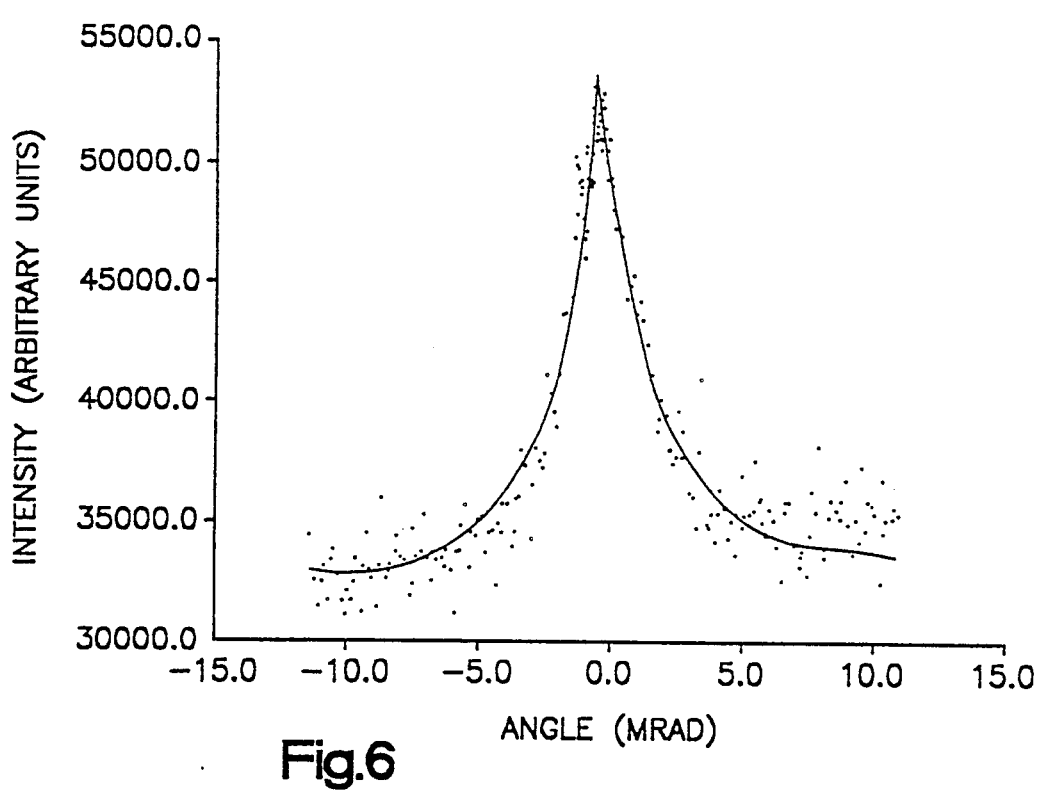
FIG. 6 is a plot of the coherent backscattering intensity for a 1% aqueous suspension of silicon carbide grains (mean diameter = 1.85 microns).
Figure 7:
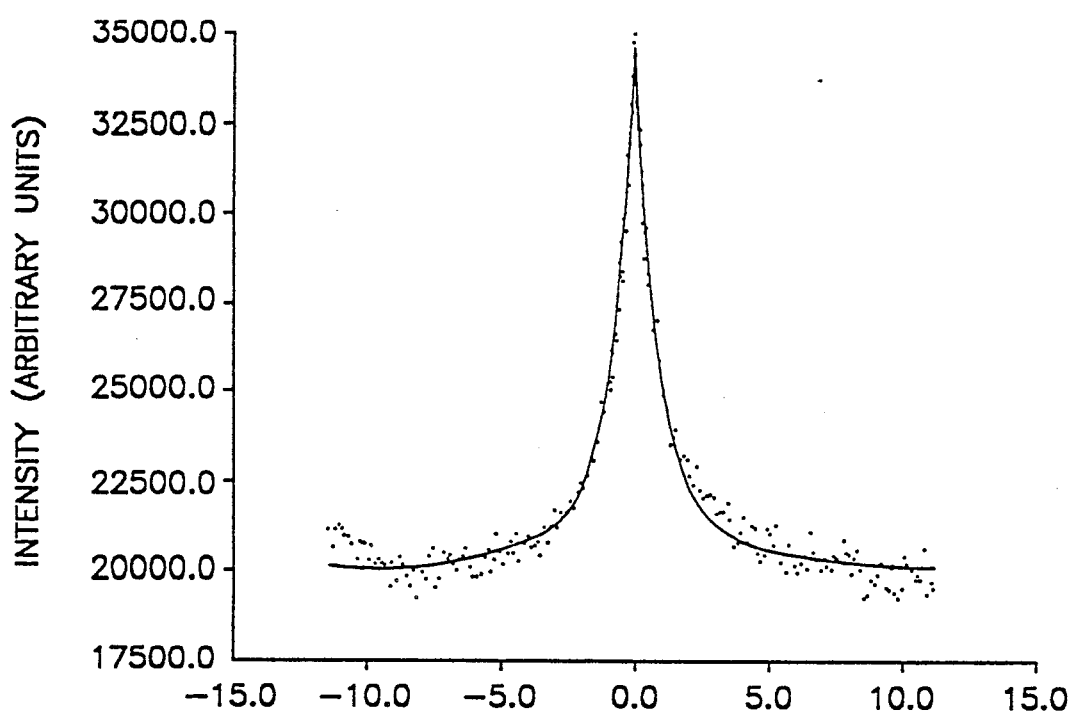
FIG. 7 is a plot of the coherent backscattering intensity for a 3% aqueous suspension of silicon carbide whiskers (mean size = 4 microns).

One area of particular interest is optically opaque slurries and suspensions. The opaqueness prevents the use of such nonintrusive techniques as bulk light scattering in the forward direction. FIG. 6 shows the coherent backscattering intensity measured from a 1% aqueous suspension of silicon carbide grains (mean diameter = 1.85 microns). FIG. 7 shows the coherent backscattering intensity measured from a 3% aqueous suspension of silicon carbide whiskers (mean size = 4 microns). As can be seen the line width shown in FIG. 6 is roughly twice that of FIG. 7. From these plots it can readily be seen that by comparing the measured line width to a data base of previously measured line widths for samples for which the concentration and particle size are known, the concentration or particle size can be determined for the sample under test (as the line width is a function of both concentration and particle size, one must be known (or constant) to determine the other). This comparison may advantageously be done in the processor 44 by mathematically comparing (e.g., lowest mean-squared-error) the measured line width to those of known samples stored in memory means associated with the processor 44 and picking the closest or by interpolating between known samples. The output 46 then consists of a signal representing the result of the comparison that is then used to control the processing of the slurry to produce or detect a desired concentration/particle size.

Figure 8:
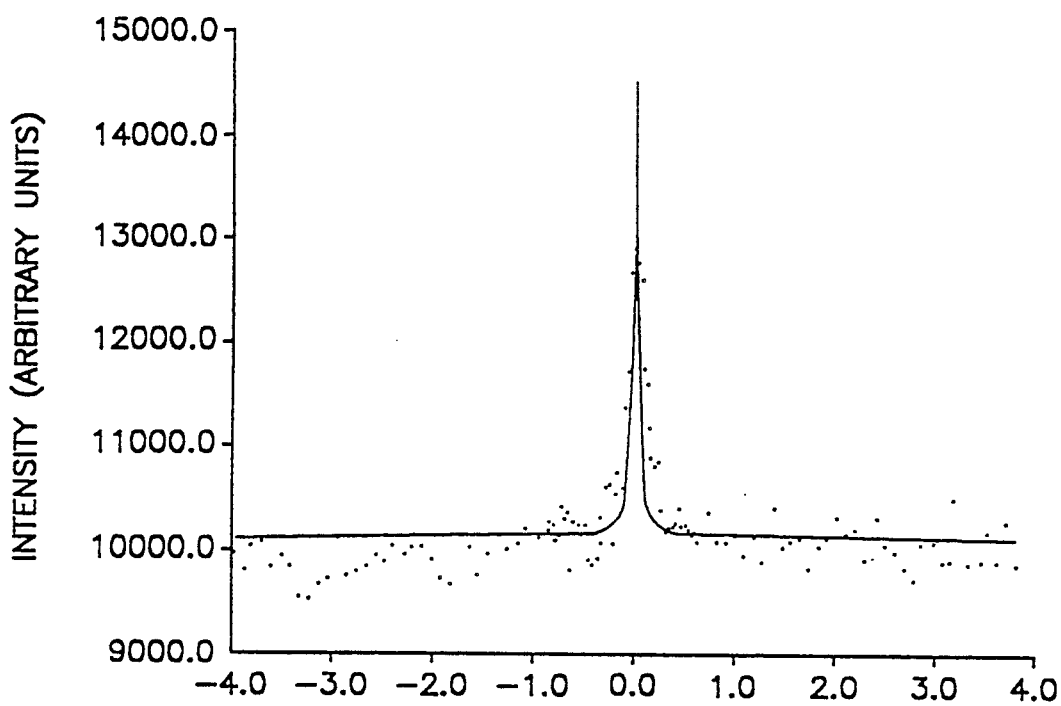
FIG. 8 is a plot of the coherent backscattering intensity for a suspension of sodium dodecyl sulfate flakes, which precipitate out of aqueous solution when the temperature is dropped below the Krafft temperature.

Coherent backscattering is also useful in detecting late stages of precipitation in a fluid where the suspension is sufficiently opaque that ordinary bulk light scattering fails. A coherent backscattering instrument would be particularly useful as a monitor in attempts to control the precipitation process (e.g., to achieve a certain desired crystal size). FIG. 8 shows a measured coherent backscattering line shape for a soap solution of sodium dodecyl sulfate (7%) and salt (3%) in which the solution was cooled and agitated to produce a precipitation of sodium dodecyl sulfate crystallites. Before the precipitation, the solution showed no coherent backscattering. In this case, the processor 44 need only detect the presence of coherent backscattering (i.e., a rise above the incoherent background level) to provide an output 46 indicating the presence of precipitation. However, as described above, it is also possible to compare the measured line shape to a data base of known samples to track the size or concentration of the precipitate.

Figure 9:
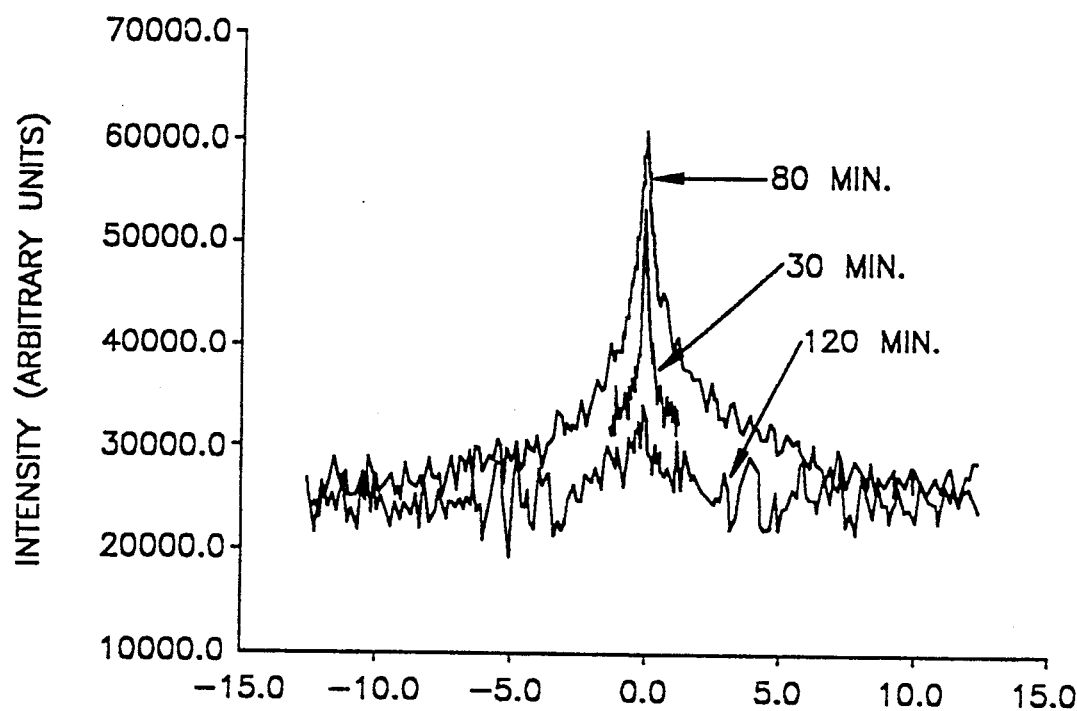
FIG. 9 is a plot of the coherent backscattering intensity for a phase-separating mixture of water and isobutyric acid (critical composition) at various times after the temperature is dropped 0.1° C. below the critical temperature.

Coherent backscatter also provides a method for detecting a fluid phase separation in a mixture of fluids. FIG. 9 shows measured coherent backscattering line shapes from a solution of isobutyric acid (39%) and water. Initially, the mixture was above 27° C. (the fluids are immiscible below 25.9° C.) and the constituents were in isotropic solution. At this time, no coherent backscattering was observed. After the temperature was dropped to 25.8° C. (but before any clearly defined meniscus developed) coherent backscattering occurred (30 minutes). With time, the line width broadened and intensified (80 minutes) (clearly defined meniscus in the sample). Finally, the coherent backscattering dropped back into the incoherent backscattering (120 minutes). Even before any visible change occurred in the mixture, the phase separation was detectable by means of coherent backscattering and even after a well-defined meniscus was visible, measurable changes were observed by coherent backscattering as occurring in the mixture. In this case, the processor 44 can simply detect the presence of backscatter to indicate phase separation or, additionally, the line width measured to provide an indication of the degree of separation. The output 46 can then be used to control/monitor, for example, chemical flows and reactions that potentially might undergo phase separation.

Figure 10:
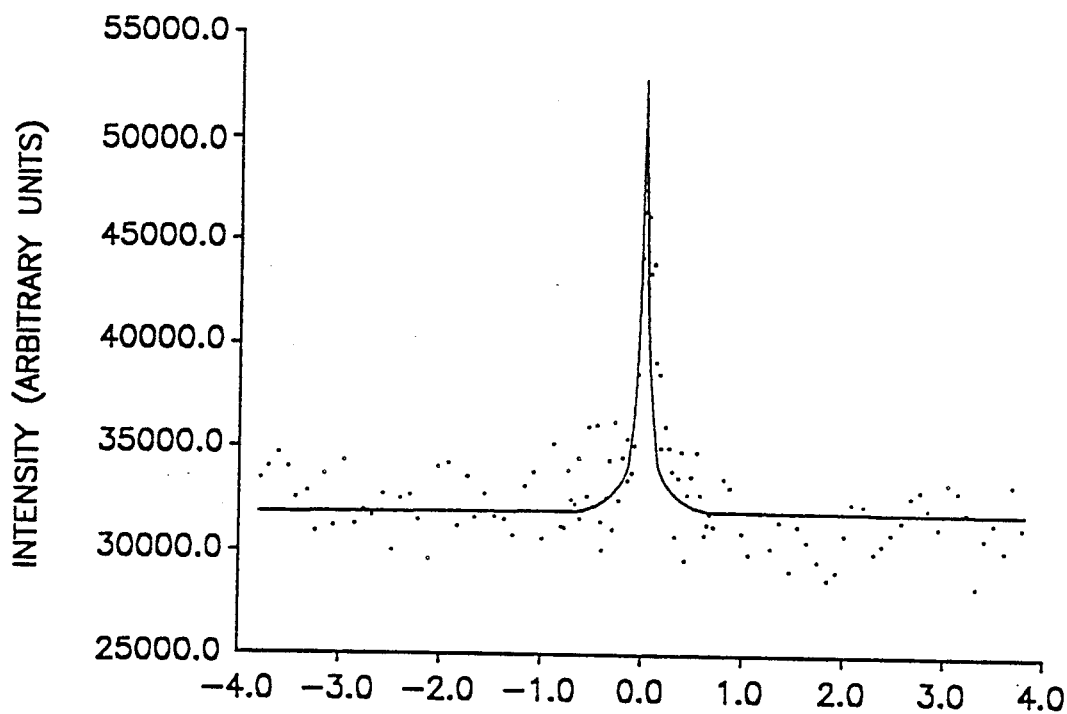
FIG. 10 is a plot of the coherent backscattering intensity for a soap solution with foam.

The presence and nature of microbubbles in a foam is also determinable using coherent backscatter. FIG. 10 shows a line shape measured from a soap foam of sodium dodecyl sulfate in aqueous solution. After vigorous shaking, a foam of soap bubbles was created and the coherent backscattering occurred. This coherent backscattering apparently occurs from microbubbles in the foam, as after about 10 minutes the coherent backscattering disappeared, even though substantial visible macrobubbles remained. By measuring the coherent backscattering intensity over a period of time, the processor 44 can indicate the initial occurrence of foam and its evolution as microbubbles collapse into large macrobubbles. The output 46 can then be used to control/monitor, for example, cavitation in fluids which are subject to severe flow conditions or external agitation. This allows correcting in real-time the external conditions giving rise to the cavitating flow.

Figure 11:
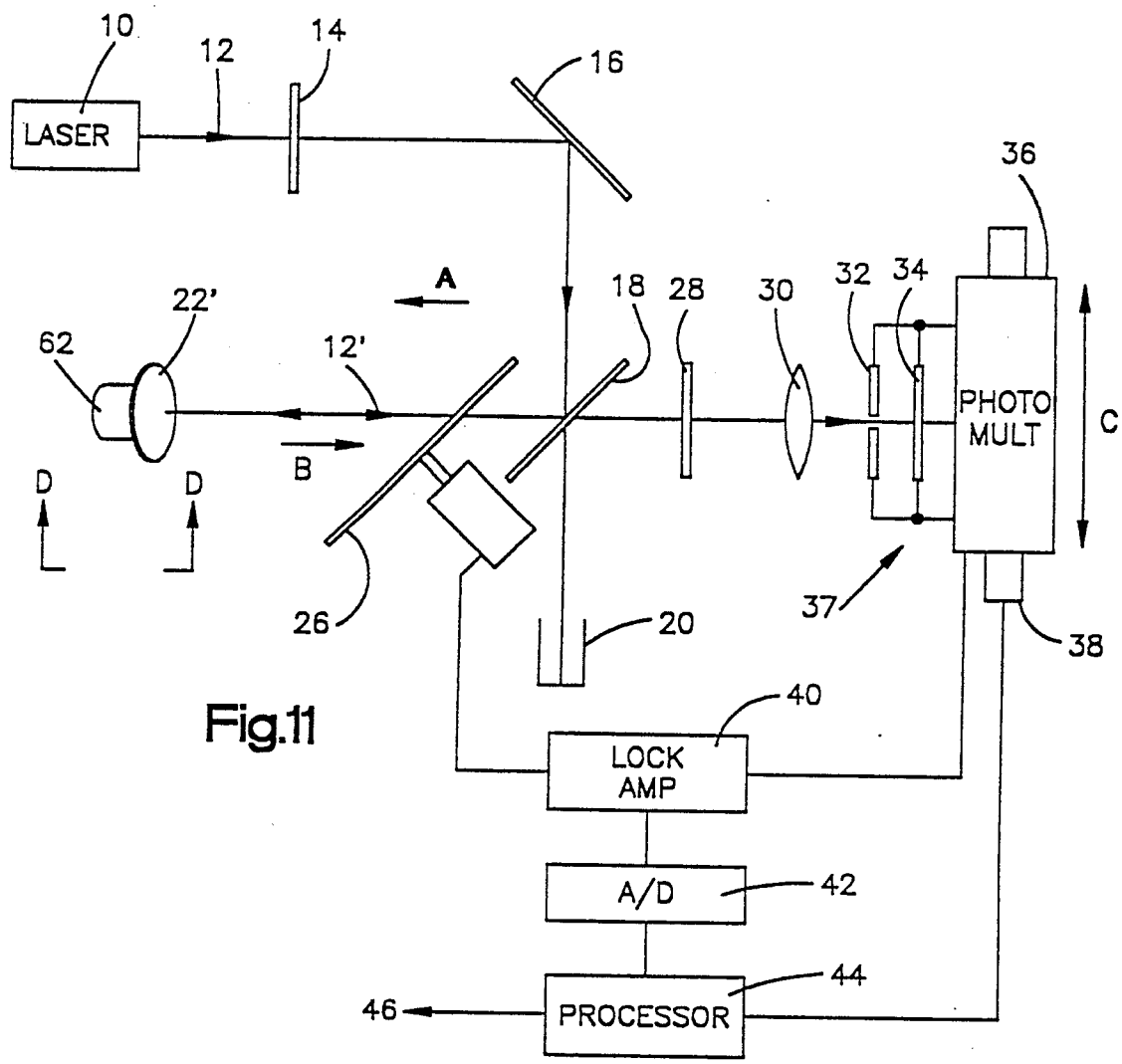
FIG. 11 is the apparatus of FIG. 3 modified to measure coherent backscattering from solids.
Figure 12:
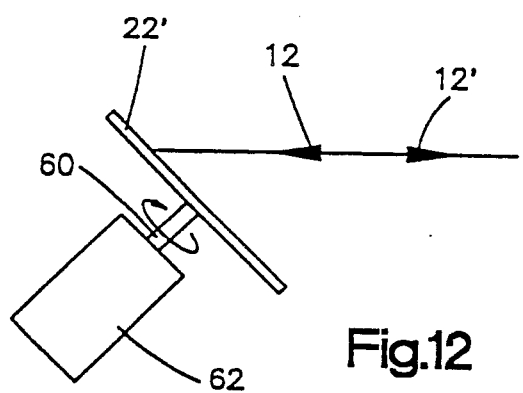
FIG. 12 is a partial view of the apparatus of FIG. 10 along line D—D.

Besides being able to monitor various solutions and suspensions based on their coherent backscattering intensity compared to that of known samples, coherent backscattering can also be used to monitor samples of solid coherent backscatterers. FIGS. 11 and 12 show the apparatus of FIG. 4 modified for solid samples. Because of spatial inhomogeneity, solid samples exhibit "speckle" that masks coherent backscatter. This speckle can be suppressed by "spatial averaging." This averaging is accomplished by rotating the sample 22' about the axis of the axle 60 driven by the motor 62 while the measurement is made. The coherent backscattering intensity can then be measured as described above.

Figure 13:
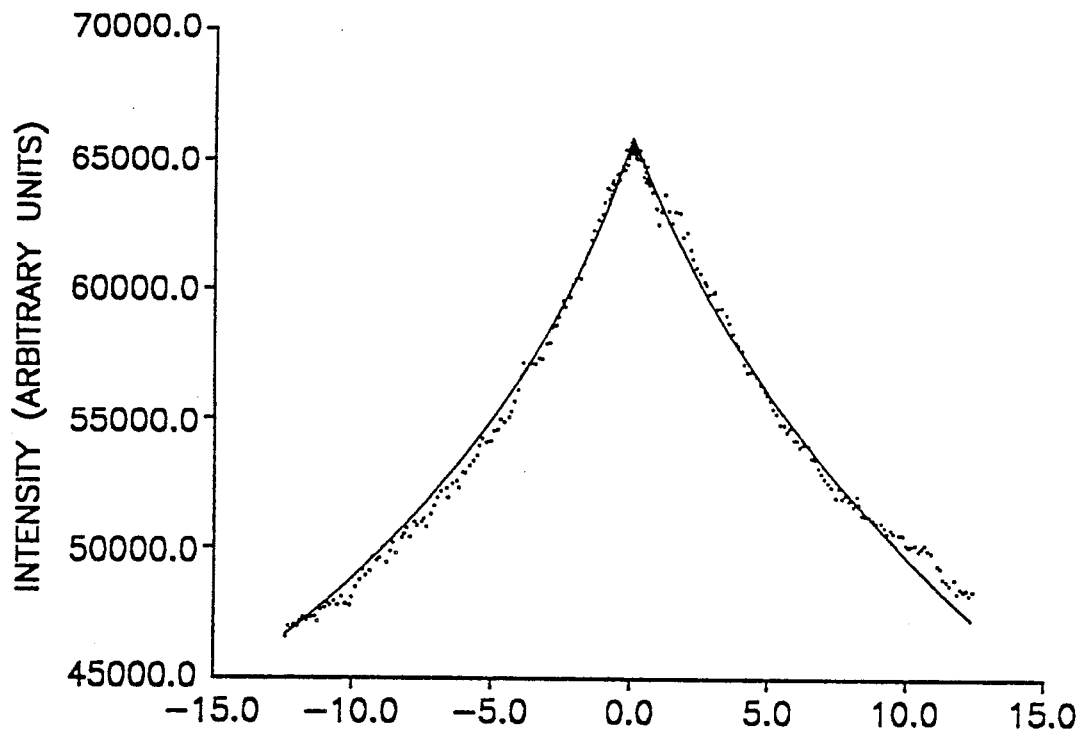
FIG. 13 is a plot of the coherent backscattering intensity for $BaSO_4$ powder (grain size $\lesssim 1$ micron).

FIG. 13 shows the coherent backscattering intensity measured from a sample consisting of a powder of $BaSO_4$ measured with the sample rotating. Powder prepared under different conditions will have different grain sizes and morphologies, resulting in different coherent backscattering profiles. Thus, if a previously identified powder is desired, whose coherent backscattering response is known, sensitivity of a processed powder to changes in processing conditions can be monitored by an on-line coherent backscattering instrument and corrections to the processing conditions can be expeditiously implemented according to the output 46.

Figure 14:
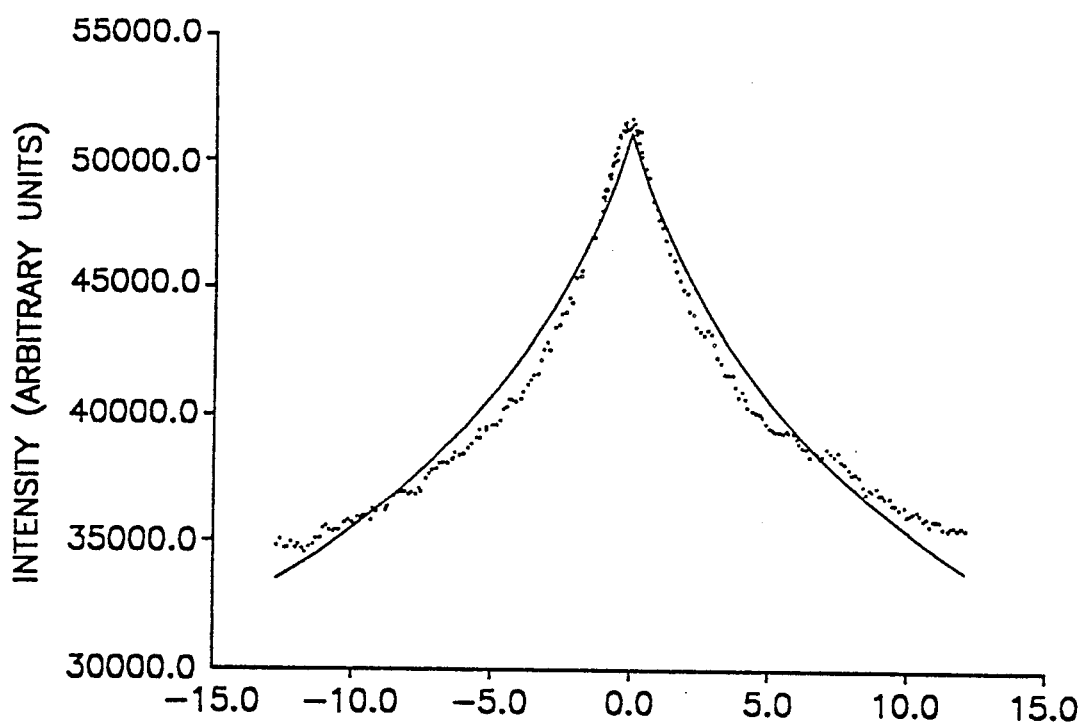
FIG. 14 is a plot of the coherent backscattering intensity for a hot-pressed (sintered) BN wafer.

FIG. 14 shows the coherent backscattering intensity of a hot-pressed (and hence sintered) wafer of BN, again measured with the sample rotating. The difference in coherent backscattering line shape of the sintered BN wafer allows it to be distinguished from the powder. In this example, while coherent backscattering is observed, the line shape is anomalous in that it is not able to be fit by the simple theoretical expression (solid-line of FIG. 14 represents the best such fit). However, samples sintered under different conditions will possess different morphologies, resulting in different coherent backscattering responses. To distinguish between samples, the processor 44 is provided with a data base of coherent backscattering line widths (or line shapes) for known samples. The measured line width is then compared to the stored values and the measured sample is identified as the closest known sample. Thus, if a previously identified sample is desired whose coherent backscattering response is known, sensitivity of the sintered sample to changes in sintering (or other processing) conditions can be monitored by an on-line coherent backscattering instrument, and corrections to the processing conditions can be expeditiously implemented in response to the output 46.

Figure 15:
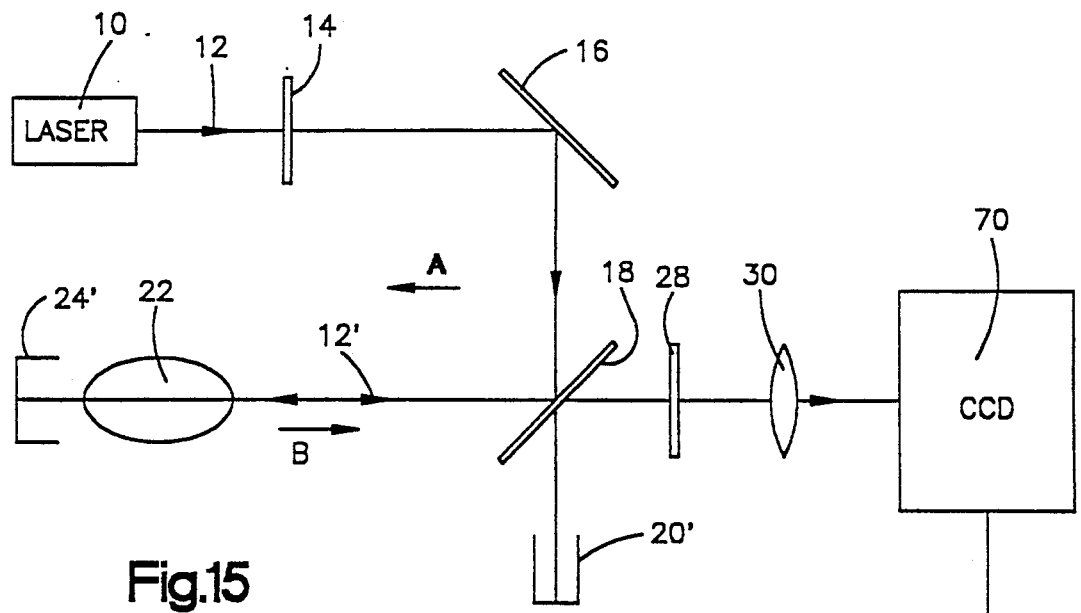
FIG. 15 is a schematic diagram of the apparatus of FIG. 4 modified to reduce data collection time by using a charge-coupled device (CCD) camera as the detector.

FIG. 15 shows an additional embodiment of an apparatus according to the invention. In place of the scanning assembly 37 of FIG. 4, a charge-coupled device camera 70 is employed in the embodiment of FIG. 15. In addition, this substitution allows the elimination of the chopper 26, lock-in amplifier 40 and A/D converter 42 of FIG. 4.

Rather than scanning the single photomultiplier 36 across the backscattering intensity, the camera 70 provides a two-dimensional digitized image of the entire backscattering intensity at a rate of, for example, 30 frames per second. In addition, the laser 10 may be of lower power, for example 10 milliwatts.

In the embodiment of FIG. 4, the beam dumps 20, 24 need only be, for example, black anodized aluminum. When the chopper 26 and lock-in amplifier 40 (and the associated synchronous detection) are eliminated as in FIG. 15, such beam dumps provide sufficient scattering to interfere with the measurement. Similarly, black felt beam dumps generate a speckle pattern at the camera 70. In the preferred embodiment of the apparatus of FIG. 15, the beam dumps 20', 24' are rotating black felt. This removes the speckle pattern.

If the scattered light is detected with the camera 70, a full two-dimensional image of the coherent backscattering cone is obtained. It is not practical to attempt to fit this full data set to the theoretical line shape. Instead, adequate results are obtained by using just a horizontal and vertical slice of the data (parallel to the plane of FIG. 15 and perpendicular thereto, respectively) through the widest portion of the backscattering cone.

These slices of data are then processed as described above for horizontal and vertical scans.

Operationally, one obtains two best values for the mean-free-path, L, one, $L^{(h)}$, from the horizontal data slice and a second, $L^{(v)}$, from the vertical data slice, with their respective standard deviations, $\sigma L^{(h)}$ and $\sigma L^{(v)}$. For a consistent determination, $L^{(h)}$ and $L^{(v)}$ should overlap with the desired confidence level.

Alternatively, one may attempt a global fit to both data sets simultaneously.

By providing backscattering data at a high rate, the camera 70 allows even faster real-time control of processes in response to the output 46.

Figure 16:
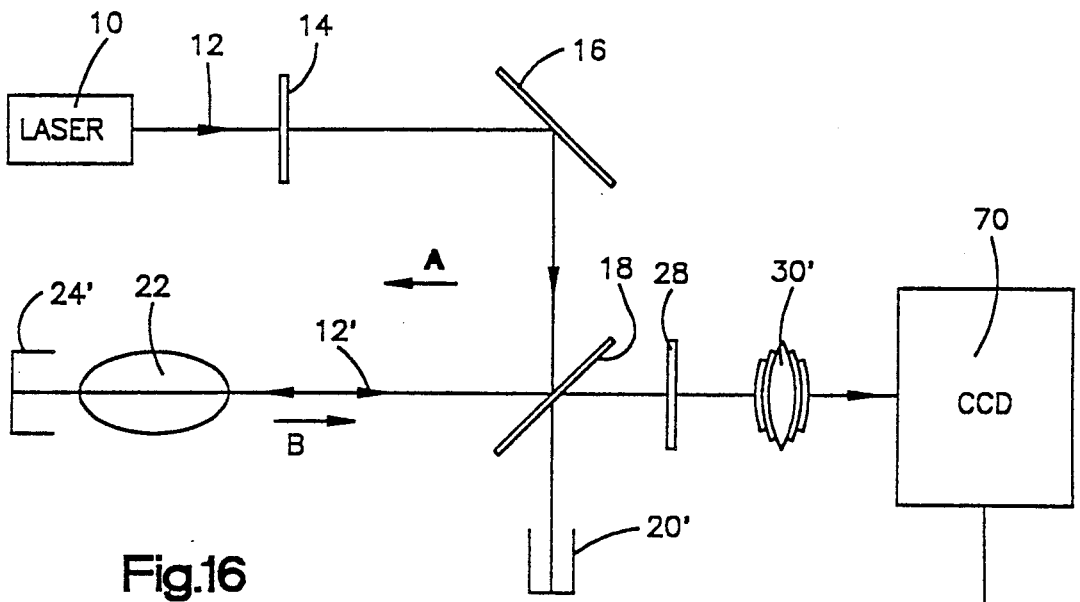
FIG. 16 is a schematic diagram of the apparatus of FIG. 4 modified with the use of a zoom lens to permit variable resolution.

FIG. 16 shows an additional embodiment of the apparatus of FIG. 15. The lens 30 is replaced by a zoom lens 30' (i.e., variable focal length lens). This allows the apparatus to have a variable resolution. For example, samples having a very narrow line shape could be better monitored with a high resolution lens setting, while samples with a broad line shape could be monitored with a low resolution lens setting.

The apparatus and methods described are not in general limited to just visible and near visible electromagnetic radiation. The techniques are adaptable as well to other areas of the electromagnetic spectrum, such as x-rays, to neutrons and to electrons.

It should be evident that this disclosure is by way of example and that various changes may be made by adding, modifying or eliminating details without departing from the fair scope of the teaching contained in this disclosure. The invention is therefore not limited to particular details of this disclosure except to the extent that the following claims are necessarily so limited.

What is claimed is:

1. A method for determining a size for particles of a known concentration in a sample of a colloidal or particulate suspension, the method comprising: illuminating the sample with a source of coherent electromagnetic radiation; measuring a coherent backscattering line shape; and computing the size by comparing the measured coherent backscattering line shape to a plurality of known coherent backscattering line shapes corresponding to known sizes.

2. A method as in claim 1, wherein said measuring and computing are performed under control of a general purpose computer.

3. A method as in claim 1, wherein said measuring and computing are performed under control of a microprocessor-based computer system.

4. A method as in claim 1, wherein said measuring step comprises chopping said source of coherent electromagnetic radiation and detecting said coherent backscattering line shape in synchronism with said chopping.

5. A method as in claim 1, wherein said measuring step comprises diffusing radiation that is coherently backscattered from said sample and detecting the diffused radiation with a photomultiplier, whereby errors due to inhomogeneity in the photomultiplier are avoided.

6. A method according to claim 1, wherein said measuring step comprises detecting radiation that is coherently backscattered with a charge-coupled device.

7. A method according to claim 1, wherein said measuring step comprises focusing radiation that is coherently backscattered on a sensor using a zoom lens, whereby the resolution of said measurement may be varied.

8. A process control apparatus comprising:
   means for illuminating a sample from a process;
   means for measuring a coherent backscattering line shape for the sample; and
   means for providing control signals to the process in response to the measured coherent backscattering line shape.

9. A process control apparatus according to claim 8, wherein said control signals are indicative of the size of particles in the sample.

* * * * *